United States Patent [19]  [11] Patent Number: 5,057,608
Wyvratt, Jr. et al.  [45] Date of Patent: Oct. 15, 1991

[54] IMMUNOREGULANTS, IMMUNOSUPPRESSANTS, PROCESS TO MAKE RING EXPANDED MACROLIDE RELATED TO FK-506/FK-520

[75] Inventors: Matthew J. Wyvratt, Jr., Mountainside; Thomas R. Beattie, Scotch Plains; Hyun O. Ok, Edison; Byron H. Arison, Watchung; Michael H. Fisher, Ringoes, all of N.J.

[73] Assignee: Merck & Co., Inc., Rahway, N.J.

[21] Appl. No.: 508,519

[22] Filed: Apr. 10, 1990

Related U.S. Application Data

[63] Continuation of Ser. No. 341,342, Apr. 21, 1989, abandoned.

[51] Int. Cl.$^5$ ............................................. C07D 498/16
[52] U.S. Cl. ...................................................... 540/456
[58] Field of Search .......................................... 540/456

[56] References Cited

FOREIGN PATENT DOCUMENTS 0184162 6/1986 European Pat. Off. ............ 540/456

Primary Examiner—Robert T. Bond
Attorney, Agent, or Firm—Robert J. North; John W. Harbour; Charles M. Caruso

[57] ABSTRACT

Ring-expanded, immunosuppressive macrolides, are produced by heating and rearranging FK-506 and related compounds.

8 Claims, No Drawings

IMMUNOREGULANTS, IMMUNOSUPPRESSANTS, PROCESS TO MAKE RING EXPANDED MACROLIDE RELATED TO FK-506/FK-520

This is a continuation of application Ser. No. 07/341,342, filed Apr. 21, 1989, now abandoned.

This invention relates to a method to produce macrolides having immunosuppressive activity. More particularly, this invention relates the thermal rearrangement of FK-506 to produce macrolides having immunosuppressive activity.

BACKGROUND OF THE INVENTION

The novel 23-membered tricyclo-macrolide, FK-506, and related compounds isolated and characterized by Tanaka, Kuroda, and co-workers, see J. Am. Chem. Soc., 109, pp. 5031, 1987, and EPO Pub. No. 0,184,162, have been shown to possess exceptional immunosuppressive activity. The potential usefulness of

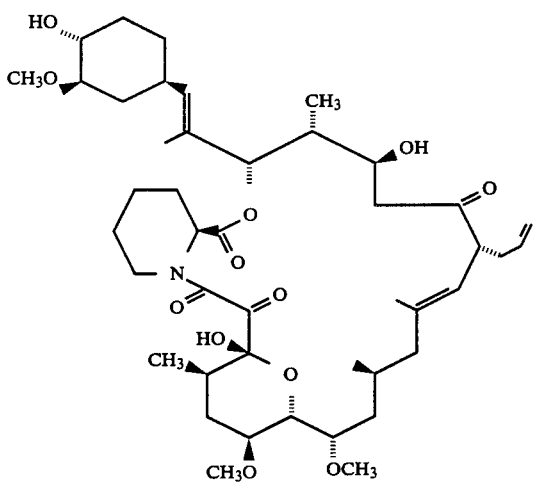

these compounds in bone marrow and organ transplantation, in the treatment of autoimmune diseases, in infectious disease treatment has been established.

SUMMARY OF THE INVENTION

Briefly, there is provided by the present invention a method to produce compounds having immunosuppressive activity of the formula;

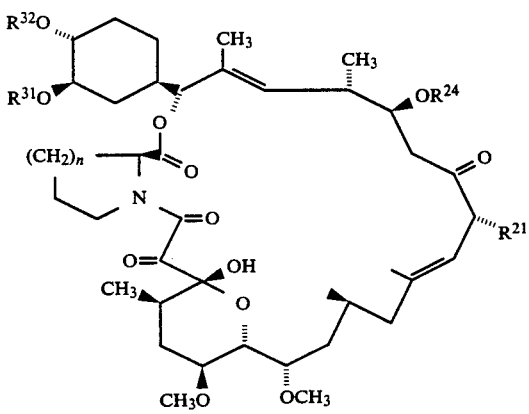

and of the formula

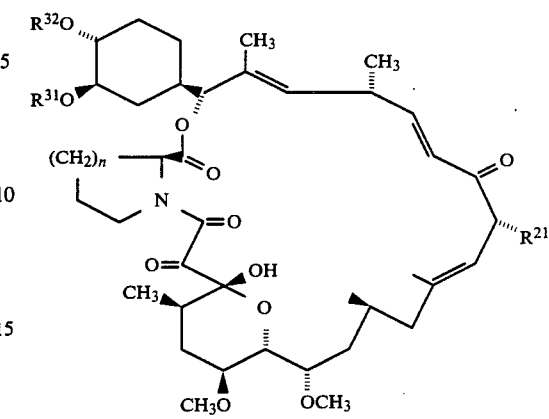

wherein $R^{21}$ is methyl, ethyl, propyl or allyl; $R^{24}$ and $R^{32}$ are, independently, hydrogen or a commonly employed hydroxyl protecting group; $R^{31}$ is hydrogen, methyl, or a hydroxyl protecting group; and n is 1 or 2.

The process herein for producing immunosuppressant compounds of formulae I and II comprises the step of heating compounds of formula III to a temperature of 130° C. to 150° C. for a time of from 1 to 48 hours in an organic solvent.

DETAILED DESCRIPTION OF THE INVENTION

FK-506 and related compounds are shown by the structural formula:

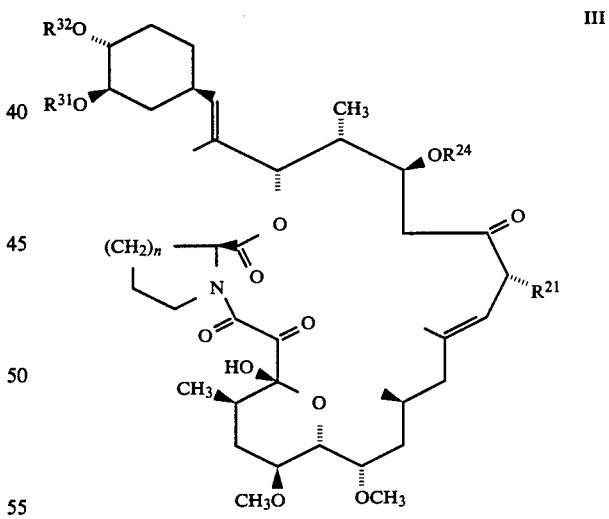

wherein $R^{21}$ is methyl, ethyl, propyl or allyl; $R^{24}$ and $R^{32}$ are, independently, hydrogen or a hydroxyl protecting group; $R^{31}$ is hydrogen, methyl or a hydroxyl protecting group; and n is 1 or 2. The production of compounds of formula (III) is well known in the literature. Both biological fermentation and synthetic processes may be found. A synthetic route to compounds of formula III may be found in U.S. Ser. No. 295,877 filed 1/11/89, to Volante, et al., hereby incorporated by reference.

Biological fermentation followed by synthetic modification is presently favored in the art as the method to produce compounds of formula (III). Organisms belonging to the genus Streptomyces such as *Streptomyces tsukubaensis*, No. 9993 and *Streptomyces hygroscopicus* No. 7238 placed in an aqueous nutrient medium will produce desired compounds in isolatable amounts. The nutrient medium contains sources of assimilable carbon and nitrogen, preferably under aerobic conditions. Produced in fermentation are four compounds of formula (III), (A) where $R^{32}$ and $R^{24}$ are hydrogen, $R^{31}$ is methyl, $R^{21}$ is allyl, and n is 2 which is FK-506; (B) where $R^{32}$ and $R^{24}$ are hydrogen, $R^{31}$ is methyl, $R^{21}$ is ethyl, and n is 2; (C) where $R^{32}$ and $R^{24}$ are hydrogen, $R^{31}$ and $R^{21}$ are methyl, and n is 2; and (D) where $R^{32}$ and $R^{24}$ are hydrogen, $R^{31}$ is methyl, $R^{21}$ is allyl, and n is 1.

A lyophilized sample of the isolated *Streptomyces Tsukubaensis* No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5, 1984), and then converted to Budapest Treaty route of the same depository on Oct. 19, 1985 under the new deposit number of FERM BP-927.

Using the four compounds produced in fermentation above, the remaining compounds of formula III may be easily produced. The allyl of $R^{21}$ may be conveniently reduced to propyl by well known methods. The hydrogen of $R^{24}$ or $R^{32}$ may be protected by well known methods. Likewise the methyl of $R^{31}$ as produced may be replaced with hydrogen or demethylated and subsequently protected as desired. This demethylation of $R^{31}$ may be carried out in a fermentation reaction using the compound of formula III as a feedstock. For instance, compound B named under formula III above may be demethylated at $R^{31}$ above by using the microorganism Actinomycetales ATCC No. 53771 as taught in U.S. Ser. No. 213,025 filed June 29, 1988 and hereby incorporated by reference. Similarly, compound A above may be demethylated as taught in U.S. Ser. No. 213,063 also filed June 29, 1988.

Suitable protecting groups for hydroxyl include those groups well known in the art which are:

1-(lower alkylthio) (lower)alkyl such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$alkylthiomethyl and the most preferred one may be methylthiomethyl;

trisubstituted silyl such as tri(lower)alkylsilyl (e.g. trimethylsilyl, triethylsilyl, tributylsilyl, tri-i-propylsilyl, tert-butyl-dimethylsilyl, tri-tert-butylsilyl, etc.), lower alkyl-diarylsilyl (e.g. methyl-diphenylsilyl, ethyl-diphenylsilyl, propyl-diphenylsilyl, tert-butyl-diphenylsily, etc.), and the like, in which the preferred one may be tri($C_1$-$C_4$)alkylsilyl and $C_1$-$C_4$alkyl-diphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

The aliphatic acyl may include lower alkanoyl which may have one or more suitable substituent(s) (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkyloxy(lower) alkanoyl which may have one or more suitable substituent(s) such as lower alkyl (e.g. cyclopropyloxyacetyl, cyclobutyloxypropionyl, cycloheptyloxybutyryl, methyloxyacetyl, methyloxypropionyl, methyloxybutyryl, methyloxyheptanoyl, methyloxyhexanoyl, etc.), and the like.

The aromatic acyl may include aroyl and substituted aroyl. Examples of aromatic acyl include benzoyl, toluoyl, xyloyl, naphthoyl, nitrobenzoyl, dinitrobenzoyl, nitronaphthoyl, etc.

The aliphatic acyl substituted with aromatic group may include ar(lower)alkanoyl which may have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and the like.

Compounds of formula III, organisms to produce the same, conditions of fermentation, separation techniques, and chemical modification of the product are fully described in EPO 0184162. This document is hereby incorporated by reference.

Flow Sheet A

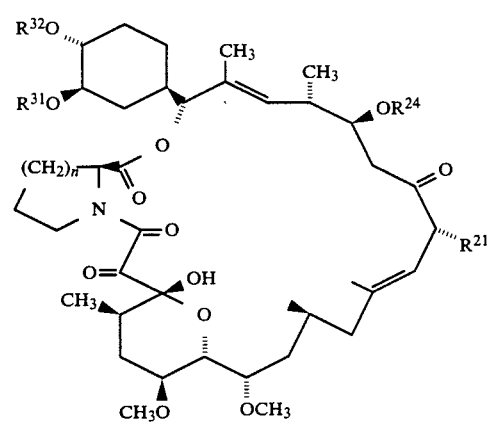

I

-continued
Flow Sheet A

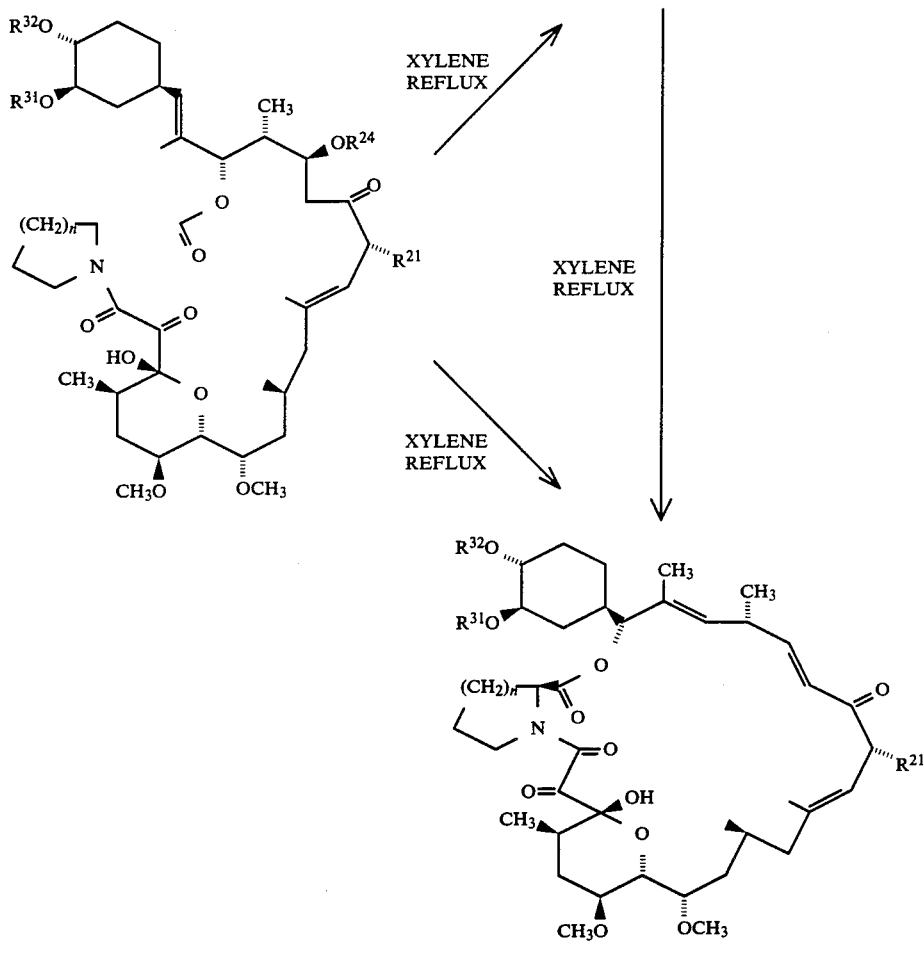

Referring to Flow Sheet A, compounds of formulae I and II, i.e. novel compounds of the instant invention, are manufactured from compounds of formula III by a new process. This process may be carried out in a single step by heating at reflux compounds of formula III in xylene for a time of from about 1 to about 48 hours. Upon heating, compounds of formula III undergo an allylic rearrangement (oxy-Cope) to give the ring-expanded macrolide compounds of formula I and its dehydrated analogs of formula II. Compounds of formula II were also obtained by heating compounds of formula I alone which suggests that dehydration may occur after rearrangement. Evidence for this rearrangement to the ring-expanded compound may be found in the NMR spectrum of compounds of formulae I and II. Therein, there should be a characteristic downfield shift of about 0.3 ppm for the $C^{28}$-H relative to its original position in the $^1$H NMR spectrum of the parent compound of formula III.

Of course, xylene as the solvent is not critical. Other organic solvents may be used at various pressures so long as approximately the reflux termperature of xylene is maintained in the heating step. A suitable temperature for heating herein ranges from about 130° C. to about 150° C. A preferred temperature ranges from about 135° to about 145° C.

Compounds of formulae I and II may be employed as immunosuppressants or antimicrobial compounds by methods and in dosages known in the prior art for compounds of formula III. Thus, these compounds are useful for the treatment and prevention of the resistance to transplantation of organs or tissues such as heart, kidney, liver, medulla ossium, skin, etc: graft-versus-host diseases by medulla ossium transplantation; autoimmune diseases such as rheumatoid arthritis, multiple sclerosis, myasthenia gravis, type I diabetes uveitis, etc.; and infectious diseases caused by pathogenic microorganisms.

The compound of this invention can be used in the form of a pharmaceutical preparation, for example, in solid, semisolid or liquid form, which contains the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing thickening and coloring agents and perfumes may be used. The active object compound is included in the pharmaceutical composition in an amount sufficient to produce the desired effect upon the process or condition of diseases.

For applying this composition to a human, it is preferable to apply it by parenteral or enteral administration. While the dosage of therapeutically effective amount of the compounds of formulae I and II varies, and also depends upon the age and condition of each individual patient to be treated, a daily dose (calculated on the basis of a 70 kg man) of about 0.01–1000 mg, preferably 0.1–500 mg and more preferably 0.5–100 mg, of the active ingredient is generally given for treating diseases. An average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention. Proton NMR spectra were recorded at 300 MHz using $CDCl_3$ as a solvent.

EXAMPLE 1

A solution of 64 mg of a compound of Formula III, $^1H$ NMR spectrum reproduced in FIG. 1, where $R^{21}$=allyl, $R^{24}$=hydrogen, $R^{31}$=methyl, $R^{32}$=hydrogen and n=2, in 3 ml of degassed xylene was heated at reflux under nitrogen for 24 hours. The reaction mixture was concentrated under reduced pressure and the residue subjected to repeated preparative thin layer chromatography on silica gel (1:4 hexanes:ether) to give 30.4 mg of the rearranged compound of formula I, $^1H$ NMR spectrum shown in FIG. 2, where $R^{21}$=allyl, $R^{24}$=hydrogen, $R^{31}$=methyl, $R^{32}$=hydrogen and n=2, 4.5 mg of the dehydrated compound of formula II where $R^{21}$=allyl, $R^{31}$=methyl, $R^{32}$=hydrogen and n=2 and 20 mg of recovered starting material. The products exhibit appropriate mass and $^1H$ NMR spectral data consistent with their structures. In addition, the structure of this product of Formula I has been confirmed by x-ray crystallographic techniques.

EXAMPLE 2

A solution of the primary thermolysis product (10 mg) of formula I where $R^{21}$=allyl, $R^{24}$=hydrogen, $R^{31}$=methyl, $R^{32}$=hydrogen and n=2 in 2 ml of degassed xylene was heated at reflux under nitrogen for 24 hours. The solution was then concentrated under reduced pressure and the residue chromatographed by preparative TLC on silica gel (5% i-PrOH/$CH_2Cl_2$) to give 3.5 mg of the dehydrated compound of formula II where $R^{21}$=allyl, $R^{31}$ methyl, $R^{32}$=hydrogen and n=2 and recovered starting material (5 mg).

EXAMPLE 3

Under a nitrogen atmosphere, 30 mg of the compound of formula III where $R^{21}$=ethyl, $R^{24}$=hydrogen, $R^{31}$=methyl, $R^{32}$=hydrogen and n=2 was dissolved in 3 ml of degassed xylene and the resulting solution heated at reflux for 24 hours. The reaction mixture was permited to cool to room temperature and then concentrated to dryness under reduced pressure. The residue was purified repeatedly by preparative TLC (silica gel, 5% i-PrOH/$CH_2Cl_2$) to give 18 mg of the compound of formula I where $R^{21}$=ethyl, $R^{24}$=hydrogen, $R^{31}$=methyl, $R^{32}$=hydrogen and n=2 and 6 mg of the dehydrated compound of formula II where $R^{21}$=ethyl, $R^{31}$=methyl, $R^{32}$=hydrogen and n=2. Mass and NMR spectral data are consistent with the structures of the products.

EXAMPLE 4

A compound (60 mg) of formula III where $R^{21}$=ethyl, $R^{24}$, $R^{31}$ and $R^{32}$=hydrogen, and n=2 is dissolved in 6 ml of degassed xylene under an inert atmosphere and heated at reflux for 24 hours. The reaction mixture is concentrated under reduced pressure and purified by preparative TLC (silica gel) to give a compound of formula I where $R^{21}$=ethyl, $R^{24}$, $R^{31}$ and $R^{32}$=hydrogen and n=2 and a compound of formula II where $R^{21}$=ethyl, $R^{31}$ and $R^{32}$=hydrogen and n=2.

EXAMPLE 5

A solution of 100 mg of a compound of formula III where $R^{21}$=allyl, $R^{24}$=hydrogen, $R^{31}$=methyl, $R^{32}$=acetyl and n=2 in 10 ml of degassed xylene is heated at reflux under nitrogen for 24 hours and then concentrated under reduced pressure. The residue is purified by preparative thin layer chromatography on silica gel (multiple elutions) to afford a compound of formula I wherein $R^{21}$=allyl, $R^{24}$=hydrogen, $R^{31}$=methyl, $R^{32}$=acetyl and n=2 and a compound of formula II wherein $R^{21}$=allyl, $R^{31}$=methyl, $R^{32}$=acetyl, and n=2.

EXAMPLE 6

After a solution of 60 mg of a compound of formula III wherein $R^{21}$=allyl, $R^{24}$=hydrogen, $R^{31}$=methyl, $R^{32}$=hydrogen and n=1 in 6 ml of degassed xylene is heated at reflux under nitrogen for 48 hours, it is concentrated under reduced pressure and purified by preparative thin layer chromatography on silica gel to give a compound of formula I wherein $R^{21}$=allyl, $R^{24}$=hydrogen, $R^{31}$=methyl, $R^{32}$=hydrogen and n=1 and a compound of formula II wherein $R^{21}$=allyl, $R^{31}$=methyl, $R^{32}$=hydrogen and n=1.

What is claimed is:

1. A method for producing immunosuppressive compounds of the formulae:

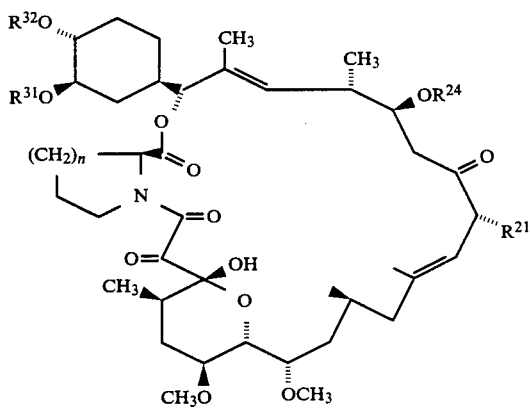

and

-continued

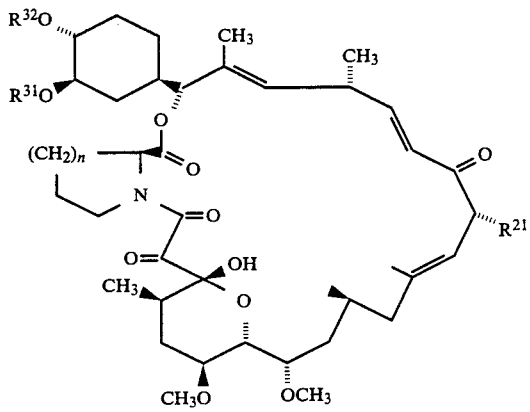

comprising the step of heating in organic solvent to a temperature of 130° to 150° C. for a time of from 1 to 48 hours a compound of the formulae:

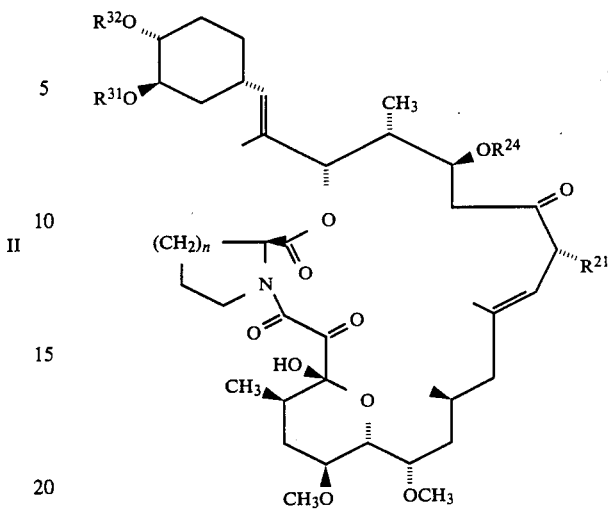

wherein $R^{21}$ is methyl, ethyl, propyl, or allyl; $R^{24}$ and $R^{32}$ are, independently, hydrogen or a protecting group for hydroxyl, $R^{31}$ is hydrogen, methyl, or a protecting group for hydroxyl; and n is 1 or 2.

2. The method of claim 1 wherein $R^{32}$ and $R^{24}$ are hydrogen, $R^{31}$ is methyl, $R^{21}$ is allyl or methyl and n is 2.

3. The method of claim 1 wherein $R^{32}$ and $R^{24}$ are hydrogen, $R^{21}$ is ethyl, $R^{31}$ is hydrogen or methyl, and n is 2.

4. The method of claim 1 wherein $R^{24}$ is hydrogen, $R^{32}$ is acetyl, $R^{31}$ is methyl, $R^{21}$ is allyl and n is 2.

5. The method of claim 1 wherein $R^{32}$ and $R^{24}$ is hydrogen, $R^{31}$ is methyl, $R^{21}$ is allyl and n is 1.

6. The method of claim 1 wherein said solvent is xylene.

7. The method of claim 1 wherein said temperature is from 135° to 145° C.

8. The method of claim 1 wherein said temperature is the reflux temperature of xylene.

* * * * *